United States Patent
Pleschke et al.

(10) Patent No.: US 7,371,861 B2
(45) Date of Patent: May 13, 2008

(54) PROCESS FOR PREPARING RING-FLUORINATED AROMATICS

(75) Inventors: Axel Pleschke, Köln (DE); Albrecht Marhold, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 385 days.

(21) Appl. No.: 11/175,612

(22) Filed: Jul. 6, 2005

(65) Prior Publication Data
US 2006/0009643 A1 Jan. 12, 2006

(30) Foreign Application Priority Data
Jul. 8, 2004 (DE) .................. 10 2004 033 525

(51) Int. Cl.
C07D 241/36 (2006.01)
C07D 471/00 (2006.01)
C07D 487/00 (2006.01)
C07C 253/00 (2006.01)

(52) U.S. Cl. ...................... 544/344; 558/343
(58) Field of Classification Search ............ None
See application file for complete search history.

(56) References Cited

U.S. PATENT DOCUMENTS

| | | | |
|---|---|---|---|
| 3,314,955 A | 4/1967 | Boudakian et al. ......... 260/251 |
| 4,287,374 A | 9/1981 | North ........................ 568/937 |
| 4,973,771 A | 11/1990 | Cantrell ..................... 568/937 |
| 6,103,659 A | 8/2000 | Pasenok et al. ............. 502/208 |
| 6,103,717 A | 8/2000 | Heinemann et al. ..... 514/229.2 |
| 6,184,425 B1 | 2/2001 | Kolomeitsev et al. ...... 570/170 |
| 2004/0144947 A1 | 7/2004 | Garayt et al. ................ 252/1 |
| 2004/0147390 A1 | 7/2004 | Schanen et al. ............ 502/150 |
| 2005/0228201 A1 | 10/2005 | Henrich et al. ............. 570/147 |

FOREIGN PATENT DOCUMENTS

DE 196 08 791 11/1997

OTHER PUBLICATIONS

Finger, et. al., Journal of Fluorine Chemistry, 1972; 1(4), 415-425.*
Pleschke A et al: "Halex reactions of aromatic compounds catalysed by 2-azaallenium, carbophosphazenium, aminophosphonium and diphosphazenium salts: a comparative study" Journal of Fluorine Chemistry, Elsevier Sequoia, Lausanne, CH, vol. 125, No. 6, Jun. 2004, pp. 1031-1038, XP004586028 ISSN: 0022-1139 p. 1035 compound 16.

Kageyama H et al: "Sulfonyl chloride as a disposable electron withdrawing substituent in halex fluorinations" Journal of Fluorine Chemistry, Elsevier Sequoia, Lausanne, CH, vol. 101, No. 1, Jan. 2000, pp. 85-89, XP004244500 ISSN: 0022-1139 the whole document.
Database CA 'Online! Chemical Abstracts Service, Columbus, Ohio, US; Kaieda, Osamu et al: "Flourinated nitrogen-containing heterocyclic compounds" XP002349763 retrieved from STN Database accession No. 1986:460633 rn 103526-69-8 abstract & JP 61 047465 A2 (Nippon Shokubai Kagaku Kogyo Co., Ltd., Japan) Mar. 7, 1986.
Database CA 'Online! Chemical Abstracts Service, Columbus, Ohio, US; Clark, D. T. et al: "Plasma polymerization. XI. A comparison of the plasma polymerization of isomeric perfluorinated diazines" XP002349764 retrieved from STN Database accession No. 1984:68864 rn 88762-12-3 abstract.
Plevey, Raymond G. et al: "Fluorinations with complex metal fluorides. Part 6. Fluorination of pyridine and related compounds with cesium tetrafluorocobaltate(III)" Journal of Fluorine Chemistry, 21(2), 159-69 Coden: JFLCAR; ISSN: 0022-1139, 1982, XP002349758 compound VI.
Yim, Moon B. et al: "Free radicals in an adamantane matrix. 13. Electron paramagnetic resonance study of .sigma.-.pi. orbital crossover in fluorinated pyridine anions" Journal of the American Chemical Society, 99(13), 4260-3 Coden: JACSAT; ISSN: 0002-7863, 1977, XP002349759 p. 4260, col. 2; example B.
Banks, Ronald E. et al: "Heterocyclic polyfluoro compounds. XIX. Synthesis of an nucleophilic substitution in some 2,4,6-trifluoropyrimidines: formation of trifluoromethylpyrimidines by pyrolysis of tetrafluoropyrimidine" Journal of the Chemical Society 'Section! C: Organic, (9), 1280-5 Coden: JSOOAX; ISSN: 0022-4952, 1970, XP000567073 p. 1283, col. 2, line 23.

* cited by examiner

Primary Examiner—Jeffrey H. Murray
(74) Attorney, Agent, or Firm—Michael A. Miller

(57) ABSTRACT

The present invention relates to an improved process for preparing ring-fluorinated aromatics of the general formula (I)

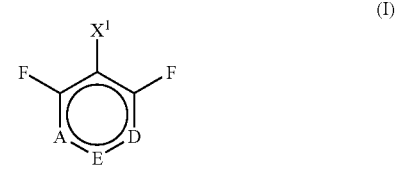

by a halogen exchange reaction (halex reaction) of a plurality of halogen substituents in one stage in the presence of a catalyst.

9 Claims, No Drawings

PROCESS FOR PREPARING RING-FLUORINATED AROMATICS

The present invention relates to an improved process for preparing ring-fluorinated aromatics by a halogen exchange reaction (halex reaction) of a plurality of halogen substituents in one stage in the presence of a catalyst.

Ring-fluorinated aromatics are important intermediates for preparing biologically active substances for pharmaceutical and agrochemical applications.

It is known to carry out halex reactions in aprotic, strongly polar solvents using metal fluorides at elevated temperature and in the presence of alkylammonium or alkylphosphonium salts (U.S. Pat. No. 4,287,374), pyridinium salts (WO 87/04149), crown ethers (DE-A 197 02 282) or tetraamidophosphonium salts (WO 98/05610). A disadvantage of such reactions is, especially when weakly activated aromatics are used, the required high reaction temperatures and long reaction times. This leads to high energy consumptions and low space-time yields. The high reaction temperatures frequently lead to the formation of undesired by-products and decomposition products. In addition, large amounts of expensive solvents are required.

In particular, the exchange of a plurality of halogen substituents of weakly activated aromatics has to date generally presented problems.

For example, it is known from EP-A 1 266 904 to subject aromatic compounds which are substituted with halogen on the ring to a halex reaction with a fluoride and at temperatures between 40 and 260° C. and in the presence of a specific catalyst. However, a disadvantage of this reaction is that especially an exchange of two and more halogen atoms in the case of weakly activated aromatics, for example tetrafluorobenzotrifluoride, necessitates at least two-stage reaction in order to keep the amount of fluoride and solvent low. Such a two-stage or multistage reaction leads not only to yield losses owing to the isolation of the intermediates but also to a relatively high level of process complexity. In 3,4-dichlorobenzonitrile, the exchange of only one chlorine substituent for fluorine is actually selective.

The preparation of 4,5,6-trifluoropyridimine by means of halex reaction has also only been described to date in the literature via the intermediate stage of 5-chloro-4,6-dipyrimidine (DE-A 196 02 095), which is in turn prepared by halex reaction from 4,5,6-trichloropyrimidine.

The exceptionally weakly activated aromatic 1,3,5-trichlorobenzene can be converted by halex reaction to 1,3,5-trichlorofluorobenzene only at temperatures of above 300° C., but a realization on the industrial scale is very costly and inconvenient and leads at these temperatures to considerable materials problems, for example stress-cracking corrosion in the case of metal tanks.

Attempts to prepare 1,3,5-trifluorobenzene starting from 1,3,5-trichlorobenzene at relatively low temperatures lead either to no formation of the desired product whatsoever (WO-A 02/092226) or only to small yields of not more than 14% (WO-A 02/092608).

Also in the case of the reaction of the weakly activated 3,4,5-trichlorobenzotrifluoride with KF, in addition to 3-chloro-4,5-difluorobenzotrifluoride as the main component, 3,4,5-trifluorobenzotrifluoride is formed merely as a by-product in a yield of distinctly below 10%.

There is thus still a need for a reaction suitable for exchanging two or more halogen substituents of weakly activated aromatics for fluorine substituents in a halex reaction, which does not have the above-detailed disadvantages of known processes and affords the corresponding ring-fluorinated aromatics in good yield.

The object on which the present invention is based is thus to provide a technically less complicated process for preparing ring-fluorinated aromatics by halogen exchange reaction (halex reaction) in good yield.

It has now been found that, surprisingly, doubly or multiply ring-fluorinated aromatics can be obtained in good yield when two or more halogen substituents in correspondingly doubly or multiply ring-halogenated weakly activated aromatics are exchanged in the presence of specific catalysts in only one reaction step.

The present invention therefore provides a process for preparing a compound of the general formula (I)

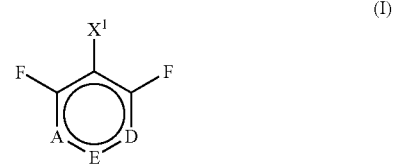

in which
A is N or CH,
D is N or CH,
E is N, CH, C—CF$_3$, C—CN or CF and
X$^1$ is H, CN or F, preferably H or F, with the proviso that A, D and E do not all simultaneously have the same definition, and preferably are not all simultaneously N or not all simultaneously CH, by reacting a compound of the general formula (II)

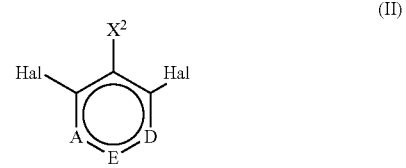

in which
A is N or CH,
D is N or CH,
E is N, CH, C—CF$_3$, C—CN or C-Hal,
X$^2$ is H, Cl, Br, I or CN, preferably H, Cl, Br or CN, more preferably H or Cl, and
Hal is Cl, Br or I, preferably Cl or Br, more preferably Cl, with the proviso that A, D and E do not all simultaneously have the same definition and are preferably not all simultaneously N or not all simultaneously CH, with a fluoride in the presence of at least one compound of the general formula (III)

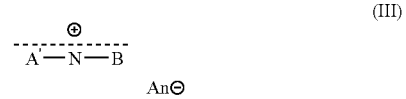

in which

A' is a radical of the formulae (IV) or (V)

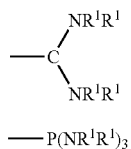

and

B, independently of A, is a radical of the formulae (IV), (V), (VIa) or (VIb)

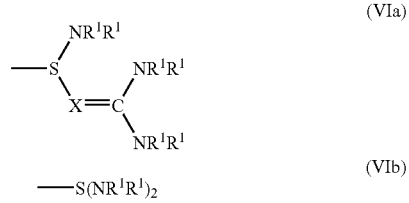

where the individual $R^1$ are the same or different and are each straight-chain or branched $C_1$-$C_{10}$-alkyl, straight-chain or branched $C_2$-$C_{10}$-alkylene or $C_6$-$C_{12}$-aryl, where one or more $NR^1R^1$ groups may also be a 3- to 5-membered, saturated or unsaturated ring which is formed from one nitrogen atom and otherwise carbon atoms, where the formula (IV) and the

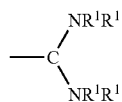

group in formula (VIa) may also be a radical of a saturated or unsaturated 4- to 8-membered ring which contains two nitrogen atoms and otherwise carbon atoms, X is N or P and $An^\ominus$ is one equivalent of an anion, characterized in that the reaction is effected in one stage.

In the context of the invention, a one-stage reaction means that there is no isolation or workup of partly fluorinated intermediates in the reaction.

The process according to the invention is preferably suitable for preparing compounds of the general formula (I) from compounds of the general formula (II) in which A and D are each N and E is CH, C—$CF_3$ or C—CN, or A and D are each CH and E is N, C—$CF_3$ or C—CN, or A is N, D is CH and E is C—$CF_3$, or A and D are each CH and E is CF in the general formula (I) and is C-Hal in the general formula (II), where Hal is as defined above for the general formula (II).

The process according to the invention is more preferably suitable for preparing 3,5-difluoropyridine, 4,5,6-trifluoropyrimidine, 1,3,5-trifluorobenzene or 3,4,5-trifluorobenzotrifluoride, in particular for preparing 4,5,6-trifluoropyrimidine, 1,3,5-trifluorobenzene or 3,4,5-trifluorobenzotrifluoride. The compounds of the general formula (II) used for this purpose are more preferably 3,5-dichloropyridine, 4,5,6-trichloropyrimidine, 1,3,5-trichlorobenzene or 3,4,5-trichlorobenzotrifluoride, in particular 4,5,6-trichloropyrimidine, 1,3,5-trichlorobenzene or 3,4,5-trichlorobenzotrifluoride.

The compounds of the general formula (II) used in the process according to the invention are weakly activated aromatics, i.e. aromatics which have a moderately electron-withdrawing group in the meta-(m-)position to at least one, preferably to at least two, of the halogen substituents to be exchanged. In the context of the invention, moderately electron-withdrawing groups, taking into account the preferable meta-arrangement with respect to at least one, preferably to at least two, of the halogens to be exchanged, are in particular nitrogen atoms in the aromatic ring and also halogen, $CF_3$ or CN substituents on a ring carbon atom, where halogen may either be Cl, Br or I, or already exchanged F.

The two $R^1$ radicals bonded to the same nitrogen atom in the general formulae (IV), (V), (VI-a) and (VI-b) are preferably identical.

The $R^1$ radicals are preferably methyl, ethyl, n-propyl, isopropyl, n-butyl, sec-butyl or tert-butyl, preferably methyl, ethyl, n-propyl or n-butyl, or an $NR^1R^1$ group is a 5- to 7-membered, saturated or unsaturated ring which is formed from one nitrogen atom and otherwise carbon atoms, or the formula (IV) or the

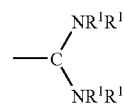

group in formula (VIa) is a saturated 5- to 7-membered ring which contains 2 nitrogen atoms and otherwise carbon atoms, X is nitrogen and $An^\ominus$ is chloride, bromide, $(CH_3)_3SiF_2^\ominus$, $HF^\ominus$, $H_2F_2^\ominus$, tetrafluoroborate hexafluorophosphate, carbonate or sulphate.

Particularly preferred compounds of the general formula (III) are compounds of the formulae (III-1) to (III-6)

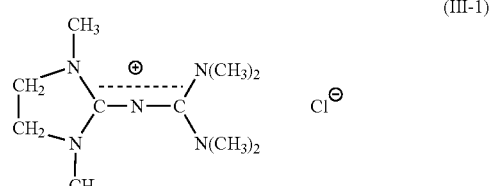

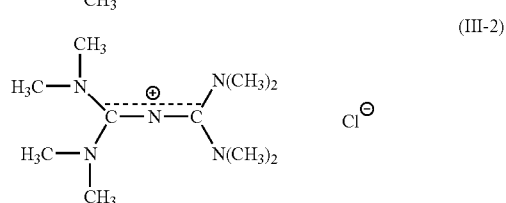

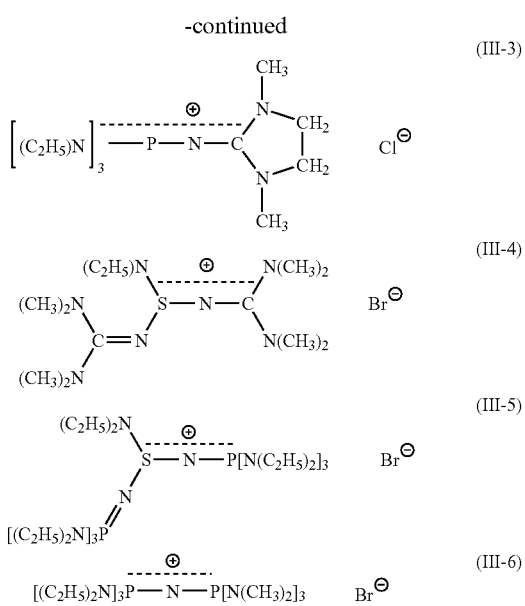

Useful fluorides for the exchange of halogen for fluorine are, for example, alkali metal, alkaline earth metal and ammonium fluorides. Preference is given to potassium fluoride, sodium fluoride, calcium fluoride and ammonium fluoride, and also to their mixtures with one another and to their mixtures with lithium fluoride, rubidium fluoride and/or caesium fluoride.

Based on 1 mol of halogen which is bonded to the ring of an aromatic compound and is to be exchanged for fluorine, for example, 0.001 to 0.5 mol, preferably 0.01 to 0.1 mol, of one or more compounds of the formula (III) and, for example, 0.8 to 2 equivalents, preferably 1.1 to 1.5 equivalents, of one or more halides can be used.

The compound(s) of the general formula (III) may be used in isolated form or in the form of solutions. Suitable solvents are, for example, dipolar aprotic and/or nonpolar aprotic solvents.

The process according to the invention is carried out preferably at temperatures in the range of 40 to 260° C., more preferably at 70 to 240° C. Very particular preference is given to 160 to 220° C. The process according to the invention can be carried out in the presence or in the absence of solvents. Preference is given to carrying out the process according to the invention in the presence of at least one solvent. Suitable solvents include, for example, dipolar aprotic and/or nonpolar aprotic solvents. Suitable dipolar aprotic solvents are, for example, dimethyl sulphoxide, sulpholane, dimethylformamide, dimethylacetamide, 1,3-dimethylimidazolin-2-one, N-methylpyrrolidone, acetonitrile and benzonitrile. Suitable nonpolar aprotic solvents are, for example, benzene, toluene, chlorobenzene, dichlorobenzenes, chlorotoluenes and chloroalkanes such as dichloromethane. The above-listed solvents are likewise suitable for the solutions of the compound(s) of the general formula (III).

Nonpolar aprotic and dipolar aprotic solvents can be used in any amounts, for example in amounts of 0.1 to 500% by weight, preferably in amounts of 0.2 to 300% by weight, based in each case on the aromatic compound used, which is substituted by halogen exchangeable for fluorine.

It is also possible to use mixtures of solvents, preference being given to using solvent mixtures which comprise 50% by weight or more dipolar aprotic solvents.

It is also possible to carry out the process according to the invention in the presence or in the absence of free-radical scavengers. Suitable free-radical scavengers are, for example, aromatic nitro compounds, preferably nitrobenzene, 3-nitrodimethylbenzamide or 1,3-dinitrobenzene, more preferably nitrobenzene or 3-nitrodimethylbenzamide. The free-radical scavengers may be used in an amount of up to 10 mol % based on the amount of the compound of the general formula (II). The use of free-radical scavengers allows the formation of by-products by dehalogenation to be distinctly reduced.

The reaction time in the process according to the invention may, for example, be in the range of 2 to 48 hours.

The process according to the invention may be carried out at reduced, standard or elevated pressure. Preference is given to working at standard pressure or elevated pressure, for example at 1 to 16 bar, more preferably at 2 to 10 bar.

In principle, the compounds of the formula (I) may be handled in the presence or absence of atmospheric oxygen. However, preference is given to handling the compounds of the formula (I) under protective gas and to carrying out the process according to the invention under protective gas. Suitable protective gases are, for example, nitrogen and argon.

The process according to the invention can be carried out batchwise or continuously.

To work up the reaction mixture present after the process according to the invention has been carried out, the procedure may be, for example, to mix the reaction mixture, after cooling, with water, remove the organic phase which forms and fractionally distil the removed organic phase under reduced pressure. The reaction mixture present after the process according to the invention has been carried out may also be subjected directly to a distillation. In addition, it is possible to add a solvent to the reaction mixture, remove solid constituents by filtration and distil the filtrate under reduced pressure. Furthermore, the product of the general formula (I) may also be removed from the reaction mixture by means of distillation under reduced pressure (pressure distillation). Other workup means can also be employed.

The preparation of the catalysts of the general formula (III) is known and is described, for example, in Synthesis 1979, 215-216, Angewandte Chemie 104, 864, 1992 or EP-A 1 266 904. In some cases, it has been observed that, in the preparation of compounds of the formula (III), mixtures of two or more individual compounds which correspond to the formula (III) are obtained. Such mixtures are also suitable as catalysts for the process according to the invention.

The process according to the invention for preparing doubly or multiply ring-fluorinated aromatics proceeds, in comparison to known processes, in one stage and thus entails, compared to the prior art, a lower level of process technology complexity with regard to materials, energy and tank lining. In addition, the target products can be obtained with at least comparable, usually higher yield compared to the prior art. The process according to the invention is therefore a distinctly improved process compared to the prior art.

The examples which follow serve to illustrate the invention by way of example and are not to be interpreted as a restriction.

EXAMPLES

Preparation of the Compound of the Formula (III-1) (CNC Catalyst)

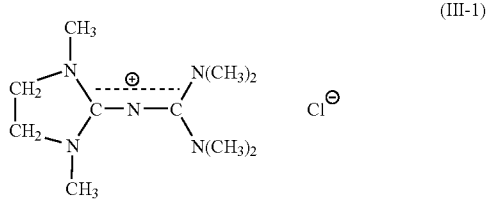

(N,N-Dimethylimidazolidino)tetramethylguanidinium chloride 600 ml of toluene were initially charged and 360 g of phosgene were added at room temperature (23° C.) within 3.5 h. Subsequently, 344 g (3.00 mol) of 1,3-dimethylimidazolidinone in 450 ml of toluene were added within 1.5 h, in the course of which the temperature was kept at 40° C. After the gas evolution had ended, excess phosgene was removed by bubbling it out with nitrogen. The suspension is filtered under inert gas and 438 g (2.56 mol) of (N,N-dimethylimidazolidino) chloride were obtained as a colourless solid. Yield: 85%. m.p.: 156-158° C.

600 ml of dichloromethane and 400 g (2.34 mol) of (N,N-dimethylimidazolidino) chloride were initially charged. Subsequently, 552 g of tetramethylguanidine (2 eq., 4.8 mol) were added with cooling within 2 hours. Subsequently, the solvent was removed and 600 ml of methanol were added to the solid residue. Afterwards, 432 g (2.4 mol) of 30% sodium methoxide solution (in methanol) were added to the suspension with cooling and the mixture is stirred at room temperature for one hour. The solvents were removed and 200 ml of dichloromethane are then added to the residue. The precipitate was filtered off and discarded. The filtrate was concentrated to dryness. 449 g (1.80 mol) of (N,N-dimethylimidazolidino)tetramethylguanidinium chloride (CNC catalyst of the formula (III-1)) were isolated. Yield: 94%; m.p.: 145-147° C.

Example 1

Preparation of 3,5-difluoropyridine

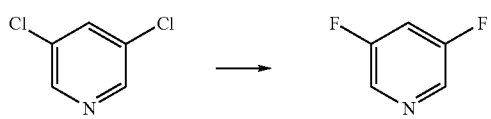

1000 g of dichloropyridine and 1580 g of dry potassium fluoride were initially charged in 1700 ml of sulpholane in an autoclave. Subsequently, 84 g of CNC catalyst (compound (III-1)) were added, nitrogen was injected to 3 bar and the mixture was heated to 205° C. with stirring for 48 h. During the reaction, a maximum total pressure of 12.4 bar arose. Subsequently, the mixture was cooled to 10° C. and the product was distilled off at standard pressure. After redistillation, 473 g of dichloropyridine (60% of theory) were obtained as a colourless liquid.

Example 2

Preparation of 4,5,6-trifluoropyrimidine

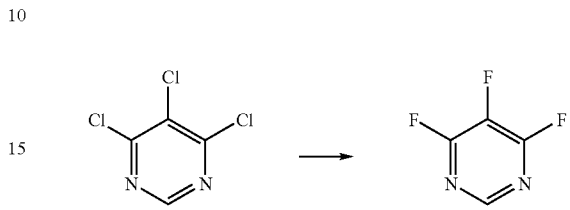

7160 ml of sulpholane and 3876 g of KF were initially charged in an autoclave and stirred at 150° C. for 1 h. Subsequently, the mixture was dried by distilling off 700 ml of sulpholane under reduced pressure. The mixture was then cooled to 90° C. and aerated with nitrogen, and a solution, heated to 45° C., of 3122 g of 4,5,6-trichloropyrimidine and 2386 g of dry sulpholane was pumped in. Afterwards, 166 g of CNC catalyst and 20.5 g of nitrobenzene were added rapidly and the vessel was sealed. The mixture was heated to 200° C. with stirring for 5 h and subsequently to 220° C. for 11 h. During the reaction, a maximum total pressure of 6.5 bar arose. The mixture was cooled to 40° C. with stirring and decompressed slowly into an ice-cooled receiver. The internal temperature was increased slowly to 150° C. and the product was distilled off initially at standard pressure, later under reduced pressure. After redistillation of the crude product, 1540 g of 4,5,6-trifluoropyrimidine (66% of theory) were obtained as a colourless liquid.

Example 3

Preparation method of 3,4,5-trifluorobenzotrifluoride

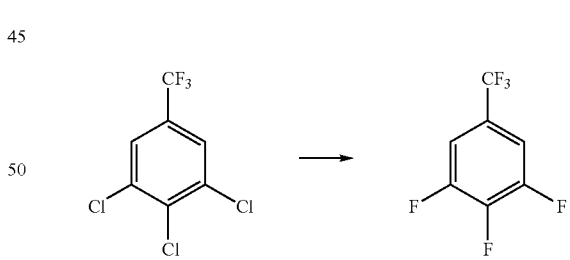

860 g of dry sulpholane and 524 g of dry KF were initially charged with exclusion of moisture in an autoclave, and 500 g of 3,4,5-trichlorobenzotrifluoride, 5 g of nitrobenzene and 25 g of CNC catalyst were added. The vessel was sealed and the mixture subsequently heated to 200° C. for 5 h and then to 220° C. for a further 12 h. During the reaction, a maximum total pressure of 9 bar arose. The mixture was then cooled to 20° C. and decompressed into a cooled receiver. The product was distilled off at standard pressure. After redistillation of the crude product, 300 g of 3,4,5-trifluorobenzotrifluoride (75% of theory) were obtained as a colourless liquid.

Example 4

Preparation method of 1,3,5-trifluorobenzene

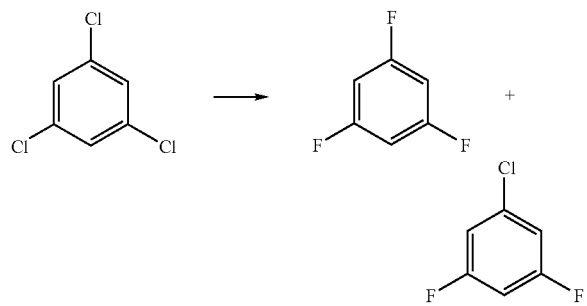

500 g of 1,3,5-trichlorobenzene, 1180 ml of sulpholane, 10.7 g of 3-nitrodimethylbenzamide and 640 g of dry KF were initially charged in an autoclave, then 48 g of CNC catalyst were added and the autoclave was sealed. The mixture was heated to 220° C. for 48 h. During the reaction, a maximum total pressure of 8 bar arose. Subsequently, the mixture was cooled to 20° C. The product was distilled off initially at standard pressure, later under reduced pressure. 310 g of a colourless liquid having a proportion of 87% by weight of 1,3,5-trifluorobenzene (74% of theory) and 8.8% by weight of difluorochlorobenzene (6.7% by weight of theory) were obtained. 1,3,5-Trifluorobenzene and difluorochlorobenzene can be separated distillatively in a known manner.

The invention claimed is:

1. Process for preparing a compound of the general formula (I)

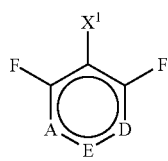

(I)

in which
  A is CH,
  D is CH,
  E is N, C—CF$_3$, C—C CF and
  X$^1$ is H, CN or F,
with the proviso that A, D and E do not all simultaneously have the same definition,
by reacting a compound of the general formula (II)

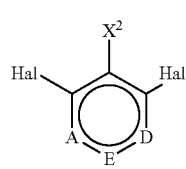

(II)

in which
  A' is CH,
  D is CH,
  E is N, C—CF$_3$, C—C C-Hal,
  X$^2$ is H, Cl, Br, I or CN and
  Hal is Cl, Br or I,
with the proviso that A, D and E do not all simultaneously have the same definition,
with a fluoride in the presence of at least one compound of the general formula (III)

(III)

in which
  A is a radical of the formulae (IV) or (V)

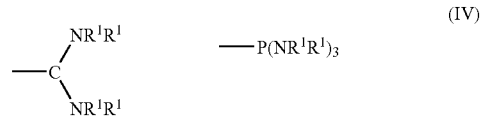

(IV)

and
  B, independently of A, is a radical of the formulae (IV), (V), (VIa) or (VIb)

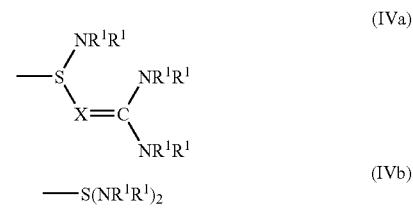

(IVa)

—S(NR$^1$R$^1$)$_2$ (IVb)

where
  the individual R$^1$ are the same or different and are each straight-chain or branched C$_1$-C$_{10}$-alkyl, straight-chain or branched C$_2$-C$_{10}$-alkylene or C$_6$-C$_{12}$-aryl,
  where one or more NR$^1$R$^1$ groups may also be a 3- to 5-membered, saturated or unsaturated ring which is formed from one nitrogen atom and otherwise carbon atoms,
  where the formula (IV) and the

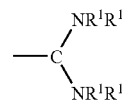

group in formula (VIa) may also be a radical of a saturated or unsaturated 4- to 8-membered ring which contains two nitrogen atoms and otherwise carbon atoms,
  X is N or P and
  An$^\ominus$ is one equivalent of an anion,
characterized in that the reaction is effected in one stage.

2. Process according to claim 1, characterized in that
  A and D are each CH and E C—CF$_3$ or C—CN, or
  A and D are each CH and E is CF in the general formula (I) and is C-Hal in the general formula (II), where Hal is as defined in claim 1.

3. Process according to claim 1, characterized in that the compound of the general formula (I) is, 1,3,5-trifluorobenzene or 3,4,5-trifluorobenzotrifluoride.

4. Process according to claim 1, characterized in that the reaction is carried out in the presence of compounds of the general formula (III) in which the $R^1$ radicals are methyl, ethyl, propyl or butyl, or an $NR^1R^1$ group is a 5- to 7-membered, saturated or unsaturated ring which is formed from one nitrogen atom and otherwise carbon atoms, or the formula (IV) or the

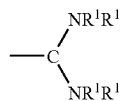

group in formula (VIa) are each a saturated 5- to 7-membered ring which contains 2 nitrogen atoms and otherwise carbon atoms,
X is nitrogen and
$An^\ominus$ is chloride, bromide, $(CH_3)_3SiF_2^\ominus$, $HF_2^\ominus$, $H_2F_2^\ominus$ tetrafluoroborate, hexafluorophosphate, carbonate or sulphate.

5. Process according to claim 1, characterized in that at least one of the compounds of the general formula (III) is a compound of the formulae (III-1), to (III-6),

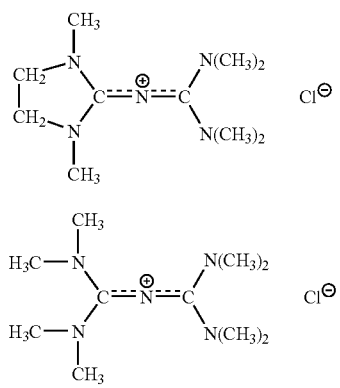

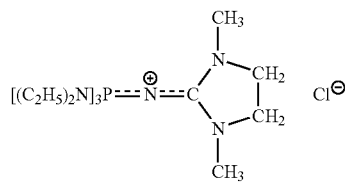

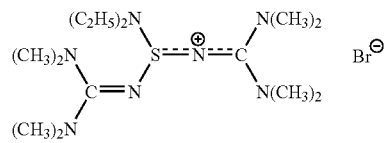

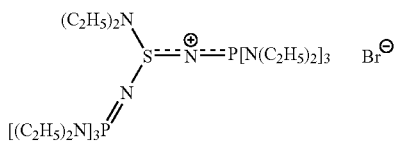

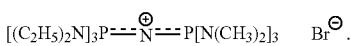

6. Process according to claim 1, characterized in that the reaction is carried out at at least a temperature of 40 to 260° C.

7. Process according to claim 1, characterized in that, based on 1 mol of halogen which is bonded to the ring of the compound of the general formula (II) and is to be exchanged for fluorine, 0.001 to 0.5 mol of one or more compounds of the formula (III) and 0.8 to 2 equivalents of one or more fluorides are used.

8. Process according to claim 1, characterized in that it is carried out in the presence of dipolar aprotic and/or nonpolar aprotic solvents.

9. Process according to claim 1, characterized in that the fluoride used is at least one alkali metal, alkaline earth metal or ammonium fluoride.

* * * * *